(12) United States Patent
Iwanczyk et al.

(10) Patent No.: US 6,377,838 B1
(45) Date of Patent: Apr. 23, 2002

(54) INTEGRAL GAMMA-RAY CAMERA AND COMPRESSION MEMBER

(75) Inventors: Jan S. Iwanczyk, Los Angeles; Bradley E. Patt, Sherman Oaks, both of CA (US)

(73) Assignee: Photon Imaging, Inc., Northbridge, CA (US)

(*) Notice: Subject to any disclaimer, the term of this patent is extended or adjusted under 35 U.S.C. 154(b) by 0 days.

(21) Appl. No.: 09/326,204

(22) Filed: Jun. 4, 1999

(51) Int. Cl.[7] .................................................. A61B 6/00
(52) U.S. Cl. ........................ 600/425; 600/431; 378/37; 250/363.02
(58) Field of Search ................................. 600/425, 431, 600/436; 250/363.02, 363.03, 363.08, 363.05; 378/37

(56) References Cited

U.S. PATENT DOCUMENTS

| | | | |
|---|---|---|---|
| 5,479,927 A | * 1/1996 | Shmulewitz | 128/660.09 |
| 5,519,221 A | 5/1996 | Weinberg | |
| 5,742,060 A | * 4/1998 | Ashburn | 250/370.09 |
| 5,773,829 A | 6/1998 | Iwanczyk et al. | |
| 5,825,031 A | * 10/1998 | Wong et al. | 250/363.03 |
| 5,965,891 A | * 10/1999 | Weinberg | 250/363.02 |
| 5,967,983 A | * 10/1999 | Ashburn | 600/436 |
| 5,999,836 A | * 12/1999 | Nelson | 600/407 |

OTHER PUBLICATIONS

Anger, Hal O., "Scintillation Camera", *The Review of Scientific Instruments*, vol. 29, No. 1 (Jan. 1958).

Baines, Cornelia J., et al., "Sensitivity and Specificity of First Screen Mammography in the Canadian National Breast Screening Study: A Preliminary Report from Five Centers", *Radiology*, vol. 160, No. 2, pp. 295–298 (Aug. 1986).

Campeau, R.J., et al., "Concordant Uptake of Tc–99m Sestamibi and TI–201 in Unsuspected Breast Tumor", *The Journal of Nuclear Medicine*, vol. 12, pp. 936–937 (Dec. 1992).

(List continued on next page.)

Primary Examiner—Marvin M. Lateef
Assistant Examiner—Eleni Mantis Mercader
(74) Attorney, Agent, or Firm—Christie, Parker & Hale, LLP

(57) ABSTRACT

A method and apparatus are provided for examining the breast for suspicious lesions. The apparatus includes a gamma-ray camera and an attachment mechanism for incorporating the gamma-ray camera as part of the breast compression fixture. The gamma-ray camera is both part of the breast compression fixture and a gamma-ray imaging system for providing an image of radiotracer distribution in the breast. The apparatus for incorporating the gamma-ray camera into the breast compression fixture assures minimum distance between the lesion in the compressed breast tissue and the gamma-ray camera. All unnecessary materials are removed from between the compressed breast and the gamma-ray camera. The apparatus also allows for positioning of the breast in different manners between the imaging sessions to obtain multiple projection views of the breast and to view the lesion with the least separation from the detector. The small camera when positioned directly against the breast allows for breast imaging without the remainder of the body in the background. The apparatus allows for the alignment of the breast and the gamma camera head in a fixed position during each imaging session. Typical views of the breast taken with the apparatus are similar to those used in mammographic projections. The attachment mechanism includes an electrical connector matching a mating connector on the mammography machine in order to enable the compression mechanism.

19 Claims, 7 Drawing Sheets

OTHER PUBLICATIONS

Khalkhali, Iraj, et al., "Tc–99m–SestaMIBI Prone Breast Imaging in Patients (PTS) with Suspicion of Breast Cancer (Ca)", *The Journal of Nuclear Medicine*, Scientific Papers, Proceedings of the 40th Annual Meeting, p. 104P (Jun. 11, 1993).

Khalkhali, Iraj, et al., "Scintimammography: The Complementary Role of Tc–99m Sestamibi Prone Breat Imaging for the Diagnosis of Breast Carcinoma", *Radiology*, vol. 196, No. 2, pp. 421–426 (1995).

Maublant, Jean C., "In Vitro Uptake of Technetium–99m–Teboroxime in Carcinoma Cell Lines and Normal Cells: Comparison with Technetium–99m–Sestamibi and Thallium–201", *The Journal of Nuclear Medicine*, vol. 34, No. 11 (Nov. 1993).

Maublant, Jean, et al., "Technetium–99m–Sestamibi Uptake in Breat Tumor and Associated Lymph Nodes", *The Journal of Nuclear Medicine*, vol. 37, No. 6, (Jun. 1996).

O'Tuama, Lorcan A., et al., "Thallium–201 Versus Technetium–99m–MIBI SPECT in Evaluation of Childhood Brain Tumors: A Within–Subject Comparison", *The Journal of Nuclear Medicine*, vol. 34, No. 7 (Jul. 1993).

Parker, Steve H., "Stereotactic Large–Core Breast Biopsy", *Percutaneous Breast Biopsy*, Raven Press, Ltd., New York (1993).

Piccolo, Sergio, "Technetium–99m–Methylene Diphosphonate Scintimammography to Image Primary Breast Cancer", *The Journal of Nuclear Medicine*, vol. 36, No. 5, pp. 718–724, (May 1995).

Short, M.D., "Gamma–Camera Systems", Nuclear Instruments and Methods in Physics Research vol. 221, pp. 142–149 (1984).

Tabár, László, et al., "Mammographic Parenchymal Pattersn", *The Journal of the American Medical Association*, vol. 247, No. 2, pp. 185–189 (Jan. 8, 1982).

Taillefer, Raymond, et al., "Technetium–99m–Sestamibi Prone Scintimammography to Detect Primary Breast Cancer and Axillary Lymph Node Involvement", *The Journal of Nuclear Medicine*, vol. 36, No. 10 (Oct. 1995).

* cited by examiner

INTEGRAL GAMMA-RAY CAMERA AND COMPRESSION MEMBER

BACKGROUND OF THE INVENTION

Radiation imaging systems typically are used to generate images of the distribution of radiation either transmitted through an object or emitted from an object. Such radiation is not visible to the naked eye. The various modalities of imaging distributions of radiation include Transmission Imaging and Emission Imaging. Both of these modalities are applied in medicine.

Classical transmission imaging or x-ray radiography is a technique wherein the radiation is generated externally and caused to propagate through an organ or body to the detector. In this way an image of the distribution of radiation absorption, or transmission, in the organ or body is obtained. One of the examples of the transmission imaging is mammography used for providing images of the breast in sufficient detail to assure high sensitivity screening for abnormal tissue.

Mammography is accepted as the best means of screening for non-palpable breast cancer. However, signatures of breast cancer, such as micro-calcifications or masses, seen for most malignant lesions, are also associated with benign processes. Thus, while the sensitivity of mammography is reported to be about 85%, its specificity is only 20–30%, and only about 30% of biopsies based on mammography are positive according to the following papers: "Tc-99m-Sesta MIBI Prone Imaging in Patients (PTS) with Suspicion of Breast Cancer (Ca)" by Khalkhali, I., I. Mena, E. Jouanne, L. Diggles, K. Alle, S. Klein in J. Nucl. Med., 24:140P, May 1993, "Sensitivity and specificity of first screen mammography in the Canadian National Breast Screening Study: a preliminary report from five centres" by Baines C J; Miller A B; Wall C; McFarlane D V; Simor I S; Jong R; Shapiro B J; Audet L; Petitclerc M; Ouimet-Oliva D; et al; in Radiology, 160:295–298, (1986), and "Mammographic parenchymal patterns: risk indicator for breast cancer?" by Tabar, L. and Dean P B, in JAMA 247:185–189, (1982).

Excisional biopsies on a false positive patient result in large unnecessary costs and the scarring that can cause difficulties in interpretation of future mammograms according to a paper titled "Radiographic Breast Anatomy: Radiological Signs of Breast Cancer" by Shaw de Paredes E. in Syllabus: A Categorical Course in Physics & Technical Aspects of Breast Imaging, eds. A. G. Haus & M. J. Yaffe, RSNA Publications, Oak Brook Ill., 1992. Many centers now use stereotactic systems for core biopsies immediately after mammography, while the breast is compressed in the same position as in the mammogram. While the stereotactic procedure is somewhat less traumatic, the cost is still significant, especially for the 70% of patients who had false positives.

In emission imaging ("Nuclear Medicine") radiation is generated within the organ by radiopharmaceutical or other radiation bearing substance which passes through or in some cases is designed to accumulate in the organ. Many emission imaging applications exist including single photon planar imaging and Single Photon Emission Computed Tomography (SPECT) for imaging the structure or function of internal organs.

Gamma-ray cameras employed in single photon emission imaging applications typically consist of a collimator for "focusing" the gamma-rays, a detector for determining the position of each incident gamma-ray and a device for displaying the acquired images. Traditional gamma-ray cameras utilize scintillation detectors coupled to photomultiplier tubes (PMT's) for detecting the light emitted from the scintillator. This development is described in a paper titled "Scintillation Camera", by Hal O. Anger, published 1958, The Review of Scientific Instruments, Vol. 29 No. 1 and in a paper titled "Gamma-Camera Systems," by M. D. Short, in 1984, Nuclear Instruments and Methods, Vol. 221. In these cameras, the scintillator is generally a single crystal (70 cm diameter) which is coupled to multiple PMT's. Each PMT covers several square centimeters of area of the scintillation crystal. Recently, smaller, higher spatial and energy resolution gamma-ray cameras dedicated to particular applications have been developed or are under development. These new cameras are based on PMT's, position sensitive PMT's (PSPMT) or solid state detectors. The solid state detector based camera can be one which has a scintillator coupled to a solid state detector. In this case the solid state detector has replaced the PMT or PSPMT as the device which converts the light emanating from the scintillator into electrical signals. A typical example of such an implementation is a gamma-ray camera based on a silicon pin photodetector array coupled to CsI(Tl) scintillator described in U.S. Pat. No. 5,773,829, which is incorporated by reference in its entirety into the present disclosure. Another approach utilizes a solid state detector, which directly converts the radiation to electrical signals.

An example of emission imaging is breast imaging using the radiopharmaceutical MiraLuma™ (Tc-99m-Sestamibi). Recent developments in testing of this radiopharmaceutical, which was initially developed for measuring blood flow in the myocardium, show that the compound is also selectively taken up in tumors, apparently in proportion to the malignancy of the tumor. The compound compares favorably with Tl-201 in tumor uptake as described in the papers titled "In vitro uptake of technetium-99m-teboroxime in carcinoma cell lines and normal cells: comparison with technetium-99m-Sestamibi and thallium-201 " by Maublant J C; Zhang Z; Rapp M; Ollier M; Michelot J; Veyre in A. J. Nuc. Med., 1993 November, 34 (11):1949 . 52, "Thallium-201 versus technetium-99m-MIBI SPECT in evaluation of childhood brain tumors: a within-subject comparison" by O'Tuama L A; Treves S T; Larar J N; Packard A B; Kwan A J; Barnes P D; Scott R M; Black P M; Madsen J R; Goumnerova L C et al. in J. Nuc. Med., 1993 July, 34(7):1045–51., and "Concordant uptake of Tc-99m Sestamibi and Tl-201 in unsuspected breast tumor" by Campeau R J; Kronemer K A; Sutherland C M, in Clin. Nucl. Med., 1992 December, 17 (12):936–7. It is believed that the Tl-201 uptake is a measure of blood flow, while the Sestamibi is sensitive to tumor metabolic rate or malignancy. In addition, Sestamibi's mechanism of uptake fixes the compound and minimizes redistribution. Uptake of Sestamibi is also very rapid. It is fixed in the heart, liver and tumor in about 10 minutes, and has a maximum uptake in the tumor at about 5 minutes. Recent reports such as the one reported in papers on detection of breast tumors using Sestamibi titled "Scintimammography: the complementary role of Tc-99 m Sestamibi prone breast imaging for the diagnosis of breast carcinoma" by I. Khalkhali, J. A. Cutrone, I. G. Mena, L. E. Dingles, et al., in Radiology 196 (1995):421–426, and "Technetium-99m-Sestamibi Prone Scinti-mammography to Detect Primary Breast Cancer and Axillary Lymph Node Involvement" by Taillefer, R., Robidoux, A., Lambert, R., Turpin, S., and Laperriere, J. in J. Nuc. Med. 36:1758, October 1995, all give sensitivities and specificities in the neighborhood of 90%. Recently, equally encouraging results were also reported for Tc-99m-Methylene Diphosphonate (MDP) with a sensitivity of 92% and a specificity of 95% in a paper titled "Technetium-99m-Methylene Diphosphonate Scintimammography to Image Primary Breast Cancer" by Piccolo, S., Lastoria, S., Mainolfi, C., Muto, P., Bazzicalupo, L., Salvatore, M. in J. Nuc. Med. 1995. 36:718–724.

Part of the 10% or so of the lesions missed in the studies such as the ones reported by Kalkhali and Taillefer cited above were due to the small size and/or lower uptake of the particular lesions. In one study reported in a paper titled "Technetium-99m-sestamibi uptake in breast tumor and associated lymph nodes" by J. Maublant, M. de Latour, D. Mestas, et al. in J. Nucl. Med. 37 (1996):922–925, patients were injected with Tc-99 m Sestamibi and imaged with a scintillation camera one day prior to a second injection of Sestamibi prior to excisional breast and/or axillary biopsy. All patients had positive mammograms, and 78% had positive scintimammograms. It was found that all excised tumor tissue had significant Tc-99 m Sestamibi uptake (6.13±2.37 tumor to tissue ratio). This included tumors missed with scintimammography. The implication is that the uptake of Tc-99 m Sestamibi is extracted into essentially all tumors and that the false negatives with Tc-99 m Sestamibi scintimammography are due to the limitations in the sensitivity, resolution and clinical placement during the procedure of current scintillation cameras. Thus, it would be desirable to provide a scintillation camera with the necessary sensitivity, resolution and clinical placement to prevent false negatives.

In emission imaging of the breast using MiraLuma™ (Tc99m-Sestamibi), 10–20 mCi of Tc-99m-Sestamibi is a typical dose as reported in papers such as the ones by Kalkhali et al. and Taillefer et al. referenced above. The resulting whole body dose is 0.3 Rad (3mGy), according to the above referenced Kalkhali paper, with minimal dose to the breast. This whole body dose is less than the dose from a standard chest X-ray and comparable to the dose from a typical mammogram. For example, a typical mammogram with a measured entrance exposure of 1 Roentgen from a Mo/Mo target/filter system at 30 kVp with a 0.36 mm aluminum HVL yields a glandular dose of 0.19 Rad (1.9mGy) as described in the Mammography Quality Control Manual, 2nd Ed., eds. R. E. Hendrick, L. Bassett, M. A. Botsco, et al., American College of Radiology 1994:159–165.

The standard scintillation camera of the prior art is too bulky to place in a position close to the breast and still image without the bulk of the body as background. Thus, the radiopharmaceutical which is fixed in the heart, liver, and other organs contributes a significant background and scattered radiation component. The background and scatter degrade the image quality. Thus, it would be desirable to provide a scintillation camera that could be placed close to the breast image without unwanted background.

In U.S. Pat. No. 5,519,221, which is incorporated by reference in its entirety into the present disclosure, the gamma-ray camera head is shown to be separated by substantial distance from the compressed breast, and additional materials such as a compression plate are placed between the breast and the gamma-ray camera head. In this reference, the gamma-ray camera is specifically separated from the immobilization apparatus in order to facilitate easy movement of the gamma-ray camera head with respect to the immobilized organ for the purpose of obtaining multiple projections. With such an apparatus, it is not possible to achieve the benefits of extreme proximity to the lesion.

For stereotactic biopsy, partial compression (10 lbs/in$^2$) is used. This typically provides compression to approximately 5 cm, which is tolerated for 30–45 minutes as described in "Chapter 7: Stereotactic large-core breast biopsy", in Percutaneous Breast Biopsy, eds. S. H. Parker, W. E. Jobe, Raven Press, Ltd., New York, 1993 by S. H. Parker. Typical full compression for standard x-ray mammography, at 18 lbs/in$^2$ is usually tolerated for only 1 minute, compressing the breast to approximately 4 cm. An example of the caudal compression is that achieved with the Instrumentarium™ mammography unit, which allows extended compression periods with little pain or trauma and still provides approximately 80% of full compression. The thickness of the partially compressed breast is approximately 2–6 cm, which is excellent for imaging with a scintillation camera. In typical use with the small gamma-ray camera one injects the patient with Tc-99m-Sestamibi and images a suspicious lesion within 10–20 minutes of the initial diagnosis.

SUMMARY OF THE INVENTION

The integral gamma-ray camera and compression member of the present invention eliminates many of the disadvantages of the prior art apparatus for examining the breast for suspicious lesions. A small gamma-ray camera is attached to a mammography unit or to a stand-alone system in such a way that the gamma-ray camera is in direct contact with the breast as part of the breast compression system. Incorporating the gamma-ray camera into the breast compression fixture assures minimum distance between the lesion in the compressed breast tissue and the gamma-ray camera. All unnecessary materials are removed from between the compressed breast and the gamma-ray camera, with the possible exception of a pad or sheet of suitable material for cushioning the breast and minimizing patient discomfort. The gamma-ray camera comprises a collimator and a gamma-ray sensitive imaging detector. The gamma-ray camera is at once a part of the means for breast compression as well as a gamma-ray imaging system for providing an image of radio tracer distribution in the breast. An example of a suitable radio tracer is the radiopharmaceutical MiraLuma™ (Tc-99m-Sestamibi).

The approach of the present invention allows for the closest distance to the lesion under examination and minimizes radiation scatter from breast tissue itself and other objects placed between the gamma-ray camera and breast. The gamma-ray camera apparatus has resolutions and signal to noise ratios that are significantly better (up to factor of 2 for resolution and greater than 60% for signal to noise) than standard scintillation cameras. This improvement in signal to noise is due to higher sensitivity and better spatial resolution achieved by the close proximity of the camera to breast lesions. In order to obtain these improvements it is important to apply the compression with the gamma-ray camera itself being part of the compression mechanism and to eliminate any additional media placed between the imaging gamma-ray camera and breast.

The proximity affords a transition from collimator limited camera resolution, which is characteristic of Anger camera imaging intended to image objects at depth, to a regime of intrinsic detector-limited resolution of relatively shallow objects which are fairly close to the detector. Thus the present invention leads to a significant improvement in spatial resolution compared to what can be obtained with the apparatus described in U.S. Pat. No. 5,519,221.

The small size of the camera and substantial improvement in geometric efficiency afforded by the proximity to the object being imaged allows the camera to be positioned for breast imaging without the remainder of the body in the background. This leads to improvements in image quality due to reduction of background and scattering due to parts of the body other than the breast.

The apparatus allows for alignment of the breast and the gamma-ray camera head in a fixed position during each imaging session. This represents an improvement over the apparatus described in U.S. Pat. No. 5,519,221 where the organ (breast) is immobilized and the gamma-ray camera head is allowed to move with respect to the immobilized organ for the purpose of obtaining multiple projections. The apparatus of the present invention allows for positioning of the breast in different manners between the imaging sessions to obtain multiple projection views of the breast and to view the lesion with the least separation from the detector. Typical views of breast taken with the apparatus are similar to those used in mammographic projections.

Because scintimammography using the apparatus of the present invention takes approximately 10 minutes to perform, the use of partial compression and newer caudal compression techniques is appropriate, thus reducing patient discomfort as compared to the use of full compression.

Because of the increased efficiency and better signal to noise ratio afforded by the apparatus of the present invention, it is possible to use lower doses of the radiopharmaceutical, or shorter image acquisition times, with equal or better image quality than is possible without the use of the subject invention.

Other features and advantages of the present invention will be apparent from the following detailed description when read in conjunction with the accompanying drawings.

BRIEF DESCRIPTION OF THE DRAWINGS

In the drawings, which constitute part of this specification, embodiments demonstrating various features of the invention are set forth as follows.

DETAILED DESCRIPTION OF THE PREFERRED EMBODIMENTS

Although detailed illustrative embodiments are disclosed herein, other suitable structures and machines for practicing the invention may be employed and will be apparent to persons of ordinary skill in the art. Consequently, specific structural and functional details disclosed herein are representative only; they describe the preferred embodiments of the invention.

Figure 1:
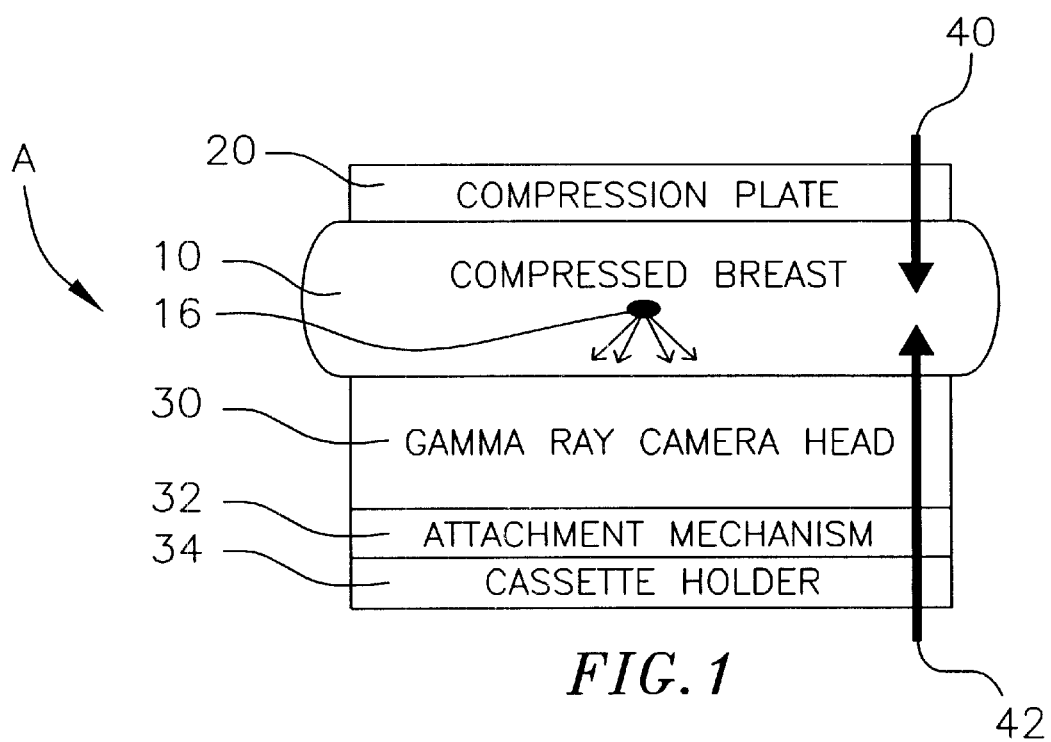
FIG. 1 is a diagrammatic side view of the present invention showing the breast compressed on one side by the mammography apparatus' compression plate and on the other by the imaging head of the gamma-ray camera.
Figure 2:
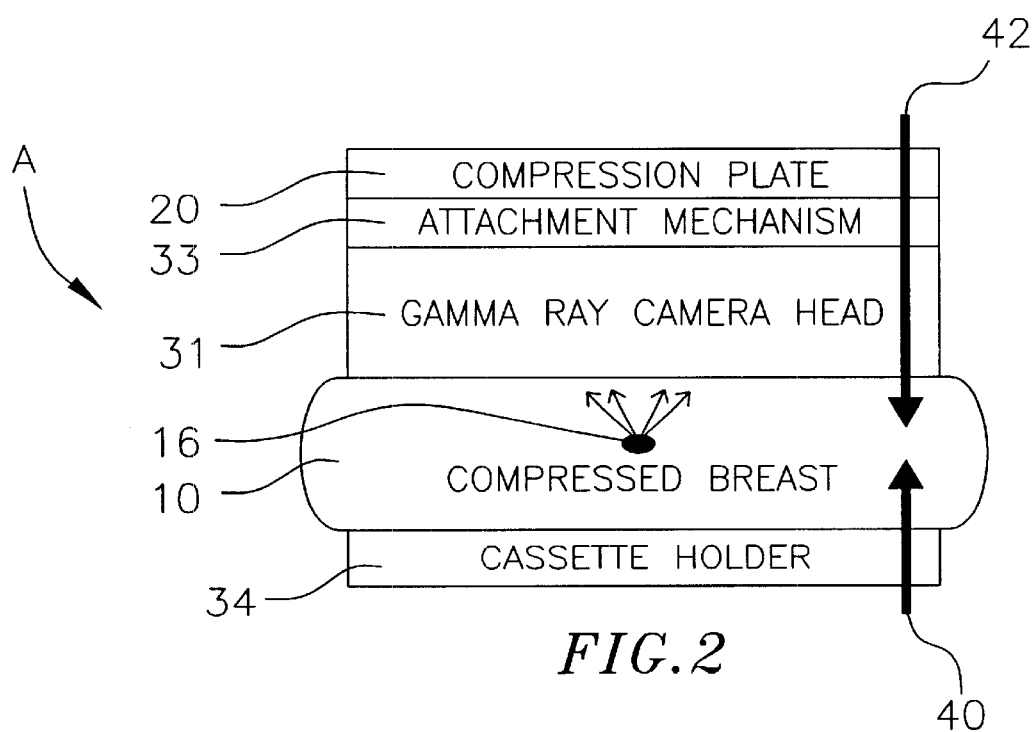
FIG. 2 is a diagrammatic side view of the present invention showing the breast compressed on one side by the mammography apparatus' cassette holder and on the other by the imaging head of the gamma-ray camera.
Figure 3:
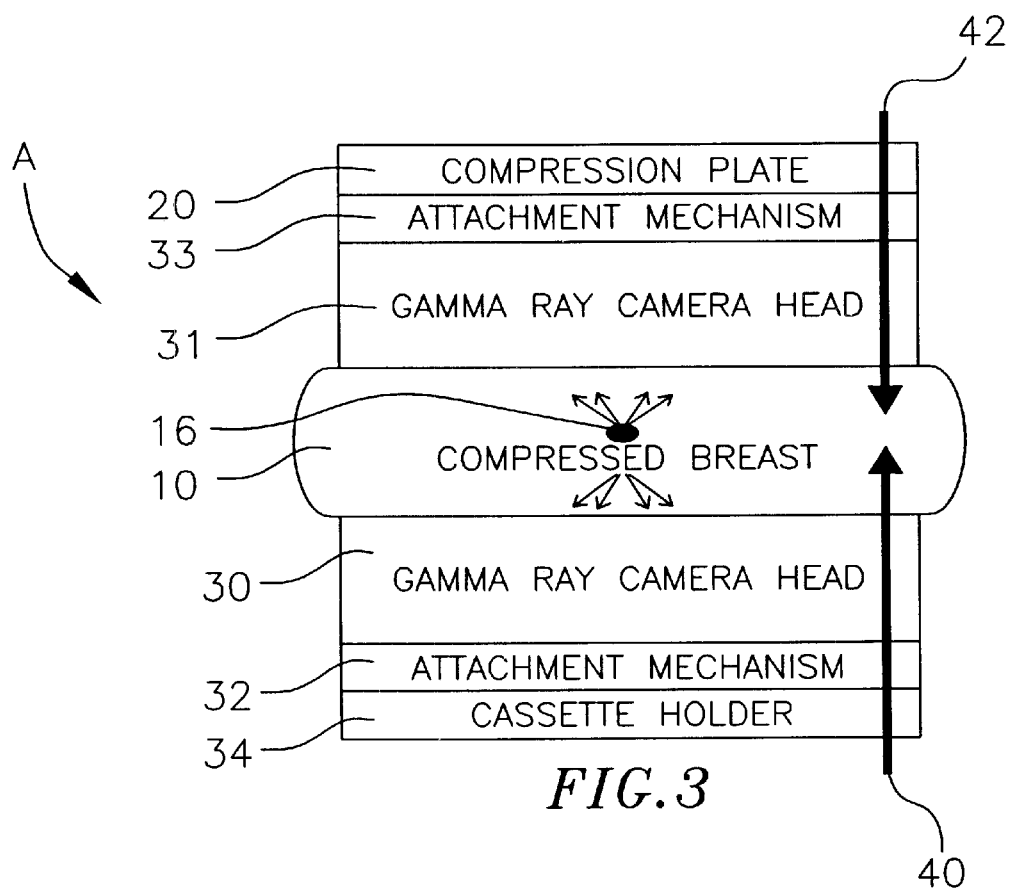
FIG. 3 is a diagrammatic side view of the present invention showing the breast compressed between two separate gamma-ray camera imaging heads.
Figure 4:
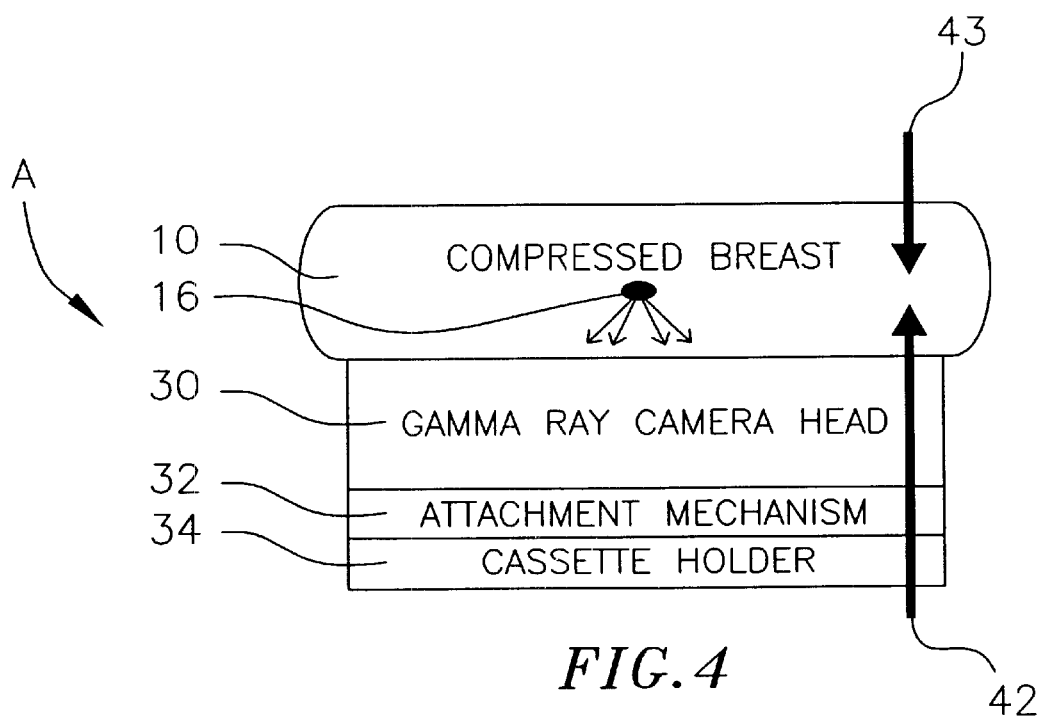
FIG. 4 is a diagrammatic side view of the present invention showing the breast compressed against the gamma-ray camera imaging h e ad by gravity.

As illustrated in FIG. 1, a breast 10 is compressed between a gamma-ray camera head 30 and a compression member or compression plate 20. FIG. 2 shows the breast 10 being compressed between a gamma-ray camera head 31 and a cassette holder 34. FIG. 3 illustrates the breast 10 being compressed between two gamma-ray camera heads 30 and 31. As illustrated in FIG. 4, the breast 10 can be compressed against the gamma-ray camera head 30 using the force of gravity alone. An attachment mechanism 32 is used to attach the gamma-ray camera head 30 to a film cassette holder 34 of a conventional mammography unit (FIGS. 1, 3 and 4). An attachment mechanism 33 is used to attach the gamma-ray camera head 31 to the compression member 20 of the conventional mammography unit (FIGS. 2 and 3). Thus, the gamma-ray camera heads 30 and 31 are part of the means for breast compression as well as the imaging system. This allows for the closest possible distance to the lesions under examination, minimizes the radiation scatter, and maximizes the resolution and signal to noise ratio.

A commercial mammography unit typically compresses a breast between a compression plate and an x-ray film cassette. X-rays pass from an x-ray generator, through the compression plate and through the compressed breast to create an image on the film in the x-ray film cassette. The x-ray film cassette houses the x-ray image receptor system including an image receptor support, an antiscatter grid, a cassette with film and screen, and an automatic exposure control detector. Rather than using x-ray film cassettes, digital x-ray image-receptor systems are sometimes used. The x-ray film cassette typically employs an attachment mechanism such as a slide and rails to allow it to be easily attached and detached from a cassette holder portion of the mammography unit.

As illustrated in FIGS. 1–4, the x-ray film cassette or digital x-ray image-receptor system is not needed for the present invention. FIGS. 1, 3 and 4 show the gamma-ray camera head 30 replaces the x-ray film cassette or digital x-ray image-receptor system of known mammography units. The compression plate and gamma-ray camera heads of FIGS. 1–4 can also be part of a dedicated unit for performing emission type imaging rather than part of a modification to a new or already existing transmission type imaging unit. As part of a dedicated unit, the various combinations of camera heads and compression plate are disposed so that the gamma-ray camera heads press directly against the breast or other body part.

Referring to FIG. 1, in an apparatus A the gamma-ray camera head 30 is attached to the cassette holder 34 via the attachment mechanism 32, and compresses the breast 10 under examination against the compression plate 20 on the opposing side of the breast 10. Compression is applied to the breast 10 in the direction shown by arrows 40 and 42. The gamma-ray camera head 30 replaces the digital or film based x-ray image-receptor systems that are part of digital mammography units. The attachment mechanism 32 differs for various manufacturers of mammography equipment so as to attach the gamma-ray camera head 30 to that particular manufacturer's cassette holder 34. After installation of the gamma-ray camera head on the mammography unit the breast is compressed between the camera and the compression plate to reduce the thickness of breast tissue during acquisition of radio tracer images. The gamma-ray camera head 30 is at once an integral part of the compression mechanism and a gamma-ray imaging system for providing an image of the radio tracer distribution in the breast 10 to image a lesion 16. This approach allows for keeping the breast and gamma-ray camera co-aligned in a well-defined and specific position with respect to the gamma-ray camera head during each imaging session.

Improvements are realized by utilizing small gamma-ray cameras, such as the one described in U.S. Pat. No. 5,773,829, offering better energy resolution (approximately 8%). This improvement is partially due to the better scatter rejection they provide. Placing the gamma-ray camera heads in direct contact with the breast 10 to minimize the distance between the gamma-ray camera heads and the lesion 16, and removing all unnecessary objects from between the gamma-ray camera heads and the lesion, serves to minimize image degrading scatter and to maximize image resolution and the signal to noise ratio.

Spatial resolution is important due to the necessity for discerning non-palpable tumors (dimensions<1 cm) for lesion diagnosis. The system spatial resolution, R is approximated by the equation $R=sqrt(Ri^2+Rc^2)$, where Ri is the intrinsic camera spatial resolution and Rc is the collimator resolution. The collimator resolution is in turn approximated by $Rc=d(L+z)/L$, where d is the collimator bore hole diameter, L is the collimator bore hole length, and z is the distance separating the source (lesion in question) from the gamma-ray entrance side of the collimator which is at the front of the gamma-ray camera head.

With the breast partially compressed against the gamma-ray camera head to a thickness of between approximately 2 cm and 6 cm, the compact nature of the apparatus of the present invention ensures that the detector is not more than 1 cm to 3 cm from any lesion. Typical values of the bore hole diameter and the bore-hole length are 1.5 mm and 2.5 cm, respectively, for a standard high resolution collimator. Using these values, the calculated improvement in spatial resolution using the apparatus of the present invention is 43% (from 5.1 mm to 2.9 mm) compared with the apparatus described in U.S. Pat. No. 5,519,221 where the lesion to detector separation is increased by a minimum of 2 inches (5.08 cm) due mainly to the additional compression plate.

FIG. 2 shows the apparatus A with the gamma-ray camera head 31 attached to the compression plate 20 via the attachment mechanism 33 to compress the breast 10 under examination against the cassette holder 34 on the opposing side of the breast 10. Compression is applied to the breast 10 in the direction shown by arrows 40 and 42. Rather than compressing the breast 10 against the cassette holder, it can be compressed against a second compression member or the film cassette.

As illustrated in FIG. 3, the compression system compresses the breast 10 between two gamma-ray camera heads 30 and 31 to reduce the thickness of the breast tissue during the acquisition of radio tracer images. The two gamma-ray cameras can provide three-dimensional images. Compression is applied in conjunction with compression mechanisms that are currently used in mammography or stand-alone systems. The two gamma-ray camera heads 30 and 31 are attached to the cassette holder 34 and compression member 20 via attachment mechanisms 32 and 33, respectively, as is done in the setups of FIGS. 1 and 2. Compression is applied to the breast 10 in the direction shown by arrows 40 and 42.

FIG. 4 illustrates the apparatus A with the gamma-ray camera head 30 attached to the cassette holder 34 via the attachment mechanism 32. The breast 10 is compressed against the gamma-ray camera head 30 using the force of gravity acting in the direction of arrow 43. The gamma-ray camera head 30 presses against the breast 10 in the direction of arrow 42. This setup allows for increased patient comfort and longer imaging times.

The gamma-ray cameras can be based on Position Sensitive Photomultiplier Tubes (PSPMT's) coupled to one or more scintillators, solid state detectors, or on standard Photomultiplier Tubes (PMT's) coupled to one or more scintillators. The present invention can also use other types of gamma-ray cameras. In addition, various radiopharmaceuticals or other radiation bearing substances can be used and different detectors can be used for detecting emissions other than gamma-rays for imaging.

The integral gamma-ray camera and compression member of the present invention can be used in compression systems for acquisition of radio tracer images from other soft organs other than breast or for acquisition of radio tracer images from small animals.

Figure 5:
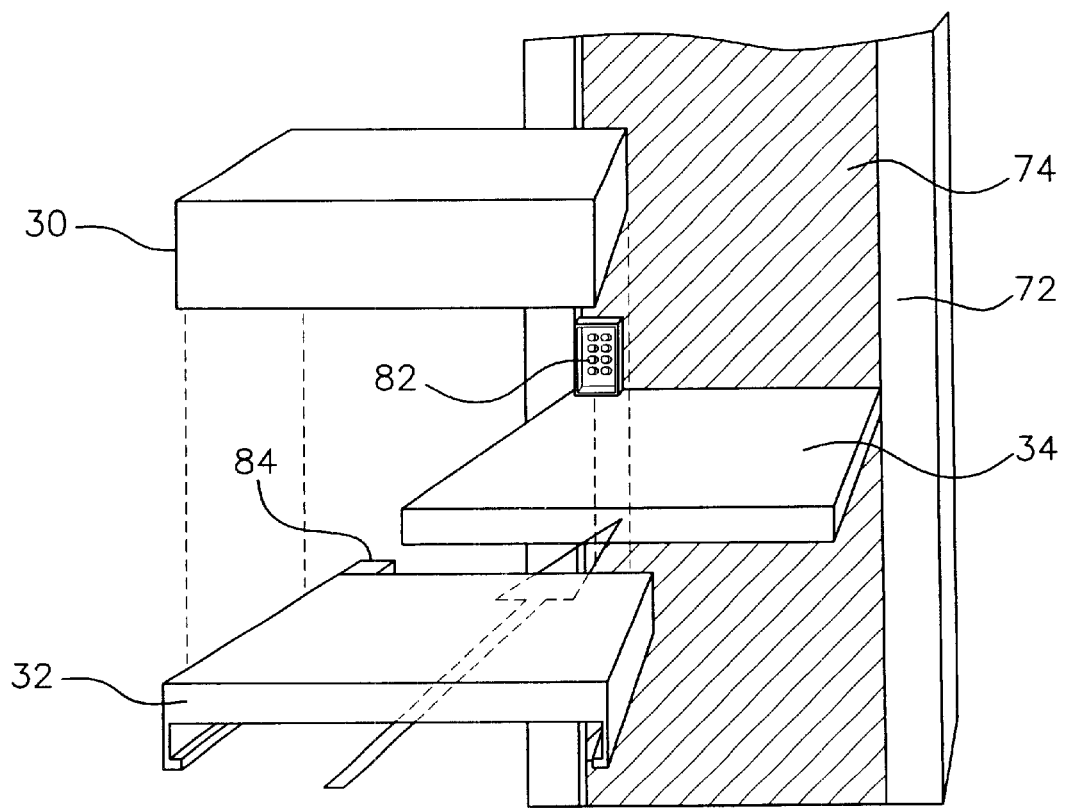
FIG. 5 is a fragmentary, exploded perspective view illustrating, in simplified form, how the gamma-ray camera attaches to an attachment mechanism which is easily attachable and detachable from the mammography unit on rails. The attachment mechanism also includes electrical connections accommodating specific requirements for different models of mammography equipment.

As illustrated in FIG. 5, the attachment mechanism 32 includes an electrical connector 84 matching a mating connector 82 on the mammography machine 72 in order to enable the compression mechanism. The electrical connections are designed to accommodate the specific requirements for different models of mammography equipment.

Figure 6:
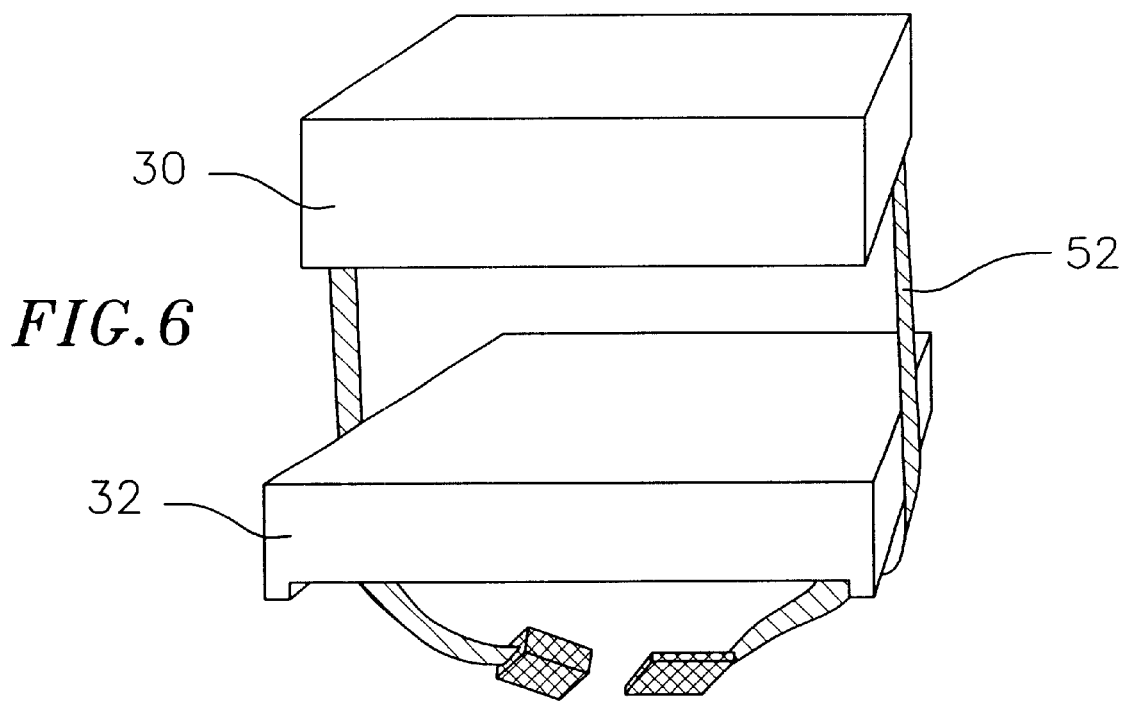
FIG. 6 is a perspective view illustrating, in simplified form, how the gamma-ray camera attaches to the mammography unit using a strap with fasteners.

As illustrated in FIG. 6, the gamma-ray camera head 30 can be attached to the attachment mechanism 32 utilizing a strap 52. The strap 52 can also be used to attach the gamma-ray camera head 30 directly to the cassette holder 34 or to the compression plate 20 of the mammography machine 72. The strap can be attached to other parts of the mammography machine 72, or to a stand-alone machine, so long as it secures the gamma-ray camera head 30 for positioning against the body part. The gamma-ray camera head 30 can alternatively be secured using rails, bolts, adhesives, or other fastening methods.

Figure 7:
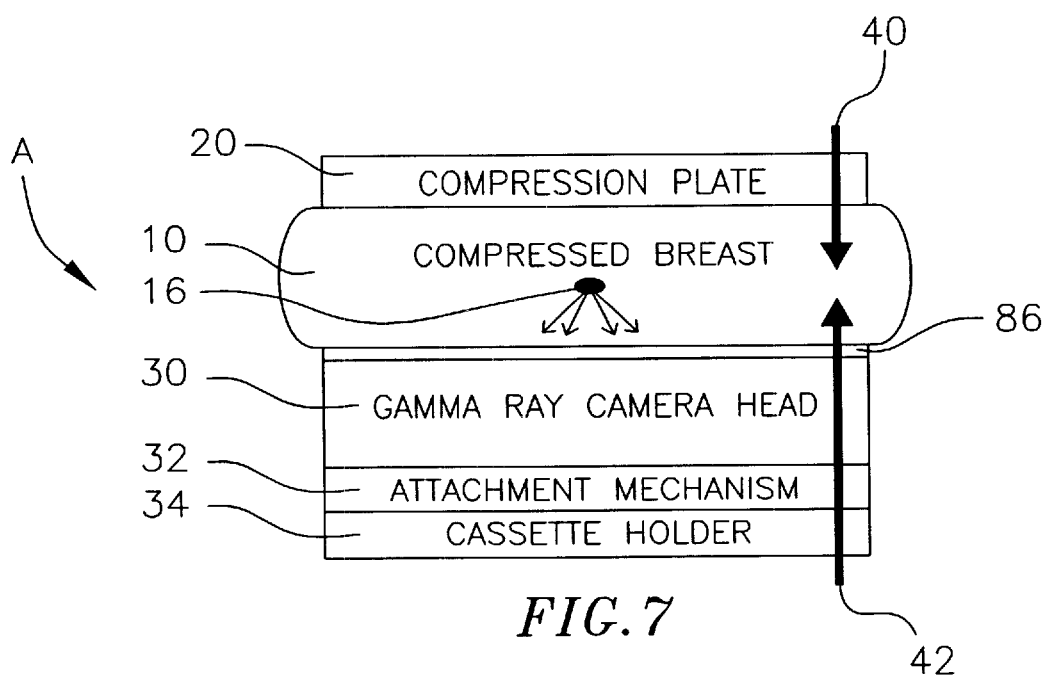
FIG. 7 is a diagrammatic side view of the present invention showing a pad or sheet for cushioning the breast and minimizing patient discomfort.

As illustrated in FIG. 7, a pad or sheet of suitable material 86 can be inserted between the breast and the gamma-ray camera head 30 for cushioning the breast and minimizing patient discomfort. For the same purpose, pads or sheets can also be inserted between the breast and the compression plate 20 of FIG. 1 or the breast and cassette holder 34 of FIG. 2. The pad or sheet 86 can be up to a few millimeters thick, and in particular 2–5 mm thick. The pad or sheet 86 should provide minimal interference with image acquisition while minimizing patient discomfort.

The apparatus in the present invention allows for positioning the breasts in different manners for the imaging sessions to obtain multiple projection views of the breast. Typical views of the breast for scintimammography are similar to those used in mammographic projections. The names for views and the abbreviated codes listed in TABLE 1 are based on the ACT Breast Imaging Reporting and Data System (ACT BI-RADS™) recommendation for standardized mammographic terminology.

TABLE 1

| VIEW | LABELING CODE |
| --- | --- |
| Mediolateral oblique | MLO |
| Carniocaudal | CC |
| 90-degree lateral | |
| Mediolateral | ML |
| Lateromedial | LM |
| Exaggerated carniocaudal | XCCL |
| Cleavage | CV |
| Axillary tail | AT |
| Tangential | TAN |

TABLE 1-continued

| VIEW | LABELING CODE |
| --- | --- |
| Roll | RL (rolled lateral) |
|  | RM (rolled medial) |
| Caudocranial | FB (from below) |
| Lateromedial oblique | LMO |
| Superolateral-to-inferomedial oblique | SIO |
| Implant displaced | ID |

The integral gamma-ray camera and compression member of the present invention is used in conjunction with known compression systems for compressing the breast 10. A radiopharmaceutical is first introduced into the patient. The breast 10 is then positioned on the gamma-ray camera head 30 as shown in FIG. 1. Then, as in commercial mammography units, compression is accomplished by a motorized mechanism with foot pedal controls enabling the technologist to use both hands to position the breasts while the foot pedals are used to apply compression. Compression is applied to the breast 10 in the direction shown by arrows 40 and 42. Manual fine-tuning can be used to adjust the final amount of compression.

Partial compression of 5–15 lbs/in$^2$ is usually applied for approximately 10 minutes while the gamma-ray camera head 30 acquires the radio tracer images. In certain cases, full breast compression of up to 18 lbs/in$^2$ can be applied for a short time. The effectiveness of compression and distance of the camera head to the examined lesions is related to how the breast is positioned and how the compression is applied, and these factors can be as important as the actual amount of compression force. For this reason in certain cases full breast compression is sometimes used.

The amount of compression and the compressed breast thickness are usually clearly displayed on the mammography unit. An automatic immediate post examination release and power failure release to minimize discomfort and ensure patient safety is usually implemented in the mammography equipment.

A similar procedure is performed when using the arrangements illustrated in FIGS. 2 and 3.

While the above description contains many specific features of the invention, these should not be construed as limitations on the scope of the invention, but rather as one exemplary embodiment thereof. Many other variations are possible. Accordingly, the scope of the invention should be determined not by the embodiments illustrated, but by the appended claims and their legal equivalents.

What is claimed is:

1. An imaging apparatus for imaging an object, whereby the object is a human body part or a small animal, the imaging apparatus comprising:
    a gamma-ray camera disposed to press against the object;
    a compression member disposed to press against the object and to compress the object between the gamma-ray camera and said compression member, wherein said compression member is a compression plate or a second gamma-ray camera;
    and an attachment mechanism for attaching said gamma-ray camera to a mammography machine.
2. The imaging apparatus of claim 1, wherein:
    said attachment mechanism attaches said imaging head to a cassette holder of said mammography machine.
3. The imaging apparatus of claim 2, wherein:
    said attachment mechanism is detachable from said cassette holder.
4. The imaging apparatus of claim 3, wherein:
    said attachment mechanism has a slide and rails for attaching to the cassette holder.
5. The imaging apparatus of claim 3, further comprising:
    an electrical connector matching a mating connector on the mammography machine in order to enable compression.
6. The imaging apparatus of claim 1, wherein:
    said attachment mechanism attaches said imaging head to a compression member of said mammography machine.
7. The imaging apparatus of claim 1, wherein:
    said gamma-ray camera is used for acquisition of radio tracer images of a lesion in a breast.
8. The imaging apparatus of claim 1, wherein:
    a pad is disposed on said imaging head for contact with said object.
9. The imaging apparatus of claim 8, wherein:
    said pad is a sheet of material between approximately 2 and approximately 5 millimeters thick.
10. An imaging apparatus for imaging a breast, the imaging apparatus comprising:
    a gamma-ray camera disposed to press against said breast in order to acquire radio tracer images of a lesion in said breast and an attachment mechanism for attaching said gamma-ray camera to a mammography machine.
11. The imaging apparatus of claim 10, wherein:
    a pad is disposed between said breast and said gamma-ray camera.
12. The imaging apparatus of claim 11, wherein:
    said gamma-ray camera has a surface disposed to support said breast against the force of gravity.
13. The imaging apparatus of claim 11, wherein:
    said attachment mechanism attaches said gamma-ray camera to a cassette holder of said mammography machine.
14. The imaging apparatus of claim 13, wherein:
    said attachment mechanism is detachable from said cassette holder.
15. The imaging apparatus of claim 14, wherein:
    said attachment mechanism has a slide and rails for attaching to the cassette holder.
16. The imaging apparatus of claim 10, further comprising:
    a first compression member disposed to directly press against said breast,
    wherein said breast is compressed between the first compression member and said gamma-ray camera, and wherein the first compression member includes a second gamma-ray camera.
17. The imaging apparatus of claim 15 wherein the gamma-ray camera and the first compression member are used to exert forces of substantially equal magnitude in opposite direction against said breast as to compress said breast.
18. A method for imaging a body part, comprising the steps of:
    attaching a gamma-ray camera to a cassette holder of a mammography machine using an attachment mechanism;
    compressing a body part between said gamma-ray camera and a compression member; and
    obtaining multiple projection views of said body part by repositioning said body part between said gamma-ray camera and said compression member between imaging sessions corresponding to each of said views.

19. The method for imaging a body part of claim 16, wherein:

said gamma-ray camera is used for acquisition of radio tracer images of a lesion in a breast.

* * * * *